United States Patent [19]
Nakao et al.

[11] Patent Number: 5,329,016
[45] Date of Patent: Jul. 12, 1994

[54] INTERMEDIATES FOR THE PREPARATION OF PHARMACEUTICAL THIOPHENE COMPOUNDS

[75] Inventors: Tohru Nakao; Yasuto Morimoto; Shuzo Takehara, all of Oita; Hiroshi Tanaka, Fukuoka, all of Japan

[73] Assignee: Yoshitomi Pharmaceutical Industries, Ltd., Osaka, Japan

[21] Appl. No.: 921,725

[22] Filed: Jul. 30, 1992

Related U.S. Application Data

[62] Division of Ser. No. 605,301, Oct. 30, 1990, Pat. No. 5,175,162.

[30] Foreign Application Priority Data

| Oct. 31, 1989 | [JP] | Japan | 1-285495 |
| Dec. 15, 1989 | [JP] | Japan | 1-326839 |
| Mar. 20, 1990 | [JP] | Japan | 2-71582 |

[51] Int. Cl.$^5$ ............................................ C07D 409/04
[52] U.S. Cl. .................................. 549/23; 546/270; 549/9
[58] Field of Search ............... 549/9, 23; 544/234; 546/270

[56] References Cited

U.S. PATENT DOCUMENTS

| 4,134,896 | 1/1979 | Sircar et al. | 549/23 |
| 4,782,057 | 11/1988 | Tahara et al. | 544/234 |
| 4,843,075 | 6/1989 | Nakao et al. | 514/248 |
| 4,849,421 | 7/1989 | Nakao et al. | 514/248 |
| 4,863,922 | 9/1989 | Baldwin et al. | 549/9 |
| 4,965,264 | 10/1990 | Nakao et al. | 544/234 |

FOREIGN PATENT DOCUMENTS

| 308515 | 3/1988 | European Pat. Off. |
| 9003380 | 4/1990 | World Int. Prop. O. |

OTHER PUBLICATIONS

T. Yakushiji et al., Br. J. Pharmacol., 98, pp. 735-640, (1989).

Primary Examiner—Richard L. Raymond
Attorney, Agent, or Firm—Sughrue, Mion, Zinn, Macpeak & Seas

[57] ABSTRACT

Thiophene compounds of the formula:

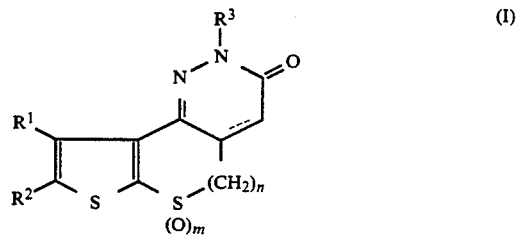

and wherein $R^1$ is hydrogen, nitro, amino, halogen or $C_{1-4}$ alkyl; $R^2$ is hydrogen, nitro, amino, halogen, $C_{1-4}$ alkyl, $C_{1-4}$ haloalkyl, acyl, $C_{2-5}$ alkoxycarbonyl, $C_{1-4}$ alkoxy-$C_{1-4}$ alkyl, aryloxy-$C_{1-4}$ alkyl, acyloxy-$C_{1-4}$ alkyl, hydroxy-$C_{1-4}$ alkyl, acyloxy-$C_{2-5}$ alkanoyl, $C_{1-4}$ alkoxy-$C_{2-5}$ alkanoyl, hydroxy-$C_{2-5}$ alkanoyl, aryloxy-$C_{2-5}$ alkanoyl or $C_{2-5}$ haloalkanoyl; $R^3$ is hydrogen, $C_{1-8}$ alkyl, hydroxy-$C_{1-4}$ alkyl, $C_{2-5}$ alkanoyloxy-$C_{1-4}$ alkyl, aryl, aryl-$C_{1-4}$ alkyl, heteroaryl, heteroaryl-$C_{1-4}$ alkyl or aryl, aryl-$C_{1-4}$ alkyl, heteroaryl or heteroaryl-$C_{1-4}$ alkyl substituted by at least one substituent selected from the group consisting of halogen, hydroxy, amino, nitro, cyano, $C_{1-4}$ alkyl, $C_{1-4}$ alkoxy, $C_{2-5}$ alkanoylamino, $C_{1-4}$ haloalkyl, acyloxy, $C_{2-5}$ alkoxycarbonyl and carboxyl on the aromatic ring; m is 0, 1 or 2; n is 1 or 2; the bond represented by ==== is a single bond or a double bond. Thiophene compounds (I) are useful as antianxiety drugs, hypnotics, antiepileptic drugs or nootropics. Thiophene compounds (II) are useful as intermediates for said thiophene compounds (I).

2 Claims, No Drawings

INTERMEDIATES FOR THE PREPARATION OF PHARMACEUTICAL THIOPHENE COMPOUNDS

This is a divisional of application No. 07/605,301 filed Oct. 30, 1990, now U.S. Pat. No. 5,175,162.

BACKGROUND OF THE INVENTION

This invention relates to thiophene compounds which are novel and useful pharmaceuticals and their pharmaceutical uses, and the synthetic intermediates therefor.

Benzodiazepine (BZP) derivatives represented by diazepam have been used as an antianxiety drug or a therapeutic medicine for sleep disturbance. The BZP receptor was discovered in 1977 [Science, vol. 198, 848 (1977)] and extensive research has been done to focus upon the mechanism of the drug's action in relation to anxiety. It has been made clear that BZP receptor ligands can differ in their allosteric modulatory effect on the gating of the $GABA_A$ receptor coupled chloride channel. It has been proposed that BZP receptor ligands which act to enhance $GABA_A$ receptor function be called BZP agonists, those which act to reduce $GABA_A$ receptor be called BZP inverse agonists, and those which neither appreciably augment nor attenuate the $GABA_A$ gating function (but can block the effects of BZP agonists and BZP inverse agonists) be called BZP antagonists. These three categories of BZP receptor ligands can be considered to have full positive, full negative, or zero intrinsic efficacy, respectively. BZP partial agonists (or BZP partial inverse agonists) exhibit intermediate intrinsic efficacy. Thus, BZP partial agonists (or BZP partial inverse agonists) bind to the BZP receptor but not all ligand-receptor complexes exert a functional effect. As a result it is possible to conceive of BZP partial agonists which, due to differential tissue receptor reserves, exhibit a more selective (e.g., anxioselective) pharmacological profile.

BZP derivatives which are used as antianxiety drugs have various effects such as sedative action, muscle-relaxation effect and potentiation action of narcotic and alcoholic effects in addition to antianxiety action. Consequently, they often cause side effects such as dizziness and sleepness. Thus, the extensive investigations are carried on to develop selective antianxiety drugs of the non-BZP types with less side effects.

Also, recently, it has been known that BZP agonists induce amnesic action [Nature, vol. 321, 864 (1986)], and the possibility has been suggested that BZP antagonists and BZP inverse-agonists are usable as nootropics since the former antagonize BZP agonists and the latter exhibit an action reverse to BZP agonists [Trends in Neurosciences, vol. 11, 13 (1988)].

In the specification of U.S. Pat. No. 4,843,075 there are disclosed useful benzothiopyrano [4,3-c]pyridazine compounds as antianxiety drugs. U.S. Pat. No. 4,849,421 discloses benzothiepino[5,4-c]pyridazine compounds which exhibit selective antianxiety activity. In particular, 2-(4-chlorophenyl)-5,6-dihydro[1]benzothiepino[5,4-c]pyridazin-3(2H)-one described in this U.S. Patent specification shows partial agonistic activity against BZP receptors and is expected clinically as a selective antianxiety drug. Further, European Patent Application No. 308,515 discloses thienocinnoline compounds useful as antianxiety drugs or antidementiac drugs.

SUMMARY OF THE INVENTION

The present inventors have conducted intensive investigations for the purpose of developing potent BZP-agonists, BZP inverse-agonists or BZP-antagonists having a non-BZP-structure which are useful pharmaceuticals and providing effective compounds and pharmaceuticals. According to such investigations, the present inventors have found that novel thiophene compounds have potent agonistic, partially agonistic or inverse agonistic actions against the benzodiazepine receptors. The present invention provides novel thiophene compounds which are pharmaceutically useful as antianxiety drugs, hypnotics, antiepileptic drugs or nootropics.

DETAILED DESCRIPTION OF THE INVENTION

The present invention relates to thiophene compounds of the formula:

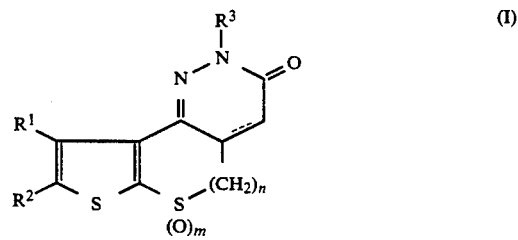

wherein $R^1$ is hydrogen, nitro, amino, halogen or $C_{1-4}$ alkyl; $R^2$ is hydrogen, nitro, amino, halogen, $C_{1-4}$ alkyl, $C_{1-4}$ haloalkyl, acyl, $C_{2-5}$ alkoxycarbonyl, $C_{1-4}$ alkoxy-$C_{1-4}$ alkyl, aryloxy-$C_{1-4}$ alkyl, acyloxy-$C_{1-4}$ alkyl, hydroxy-$C_{1-4}$ alkyl, acyloxy-$C_{2-5}$ alkanoyl, $C_{1-4}$ alkoxy-$C_{2-5}$ alkanoyl, hydroxy-$C_{2-5}$ alkanoyl, aryloxy-$C_{2-5}$ alkanoyl or $C_{2-5}$ haloalkanoyl; $R^3$ is hydrogen, $C_{1-8}$ alkyl, hydroxy-$C_{1-4}$ alkyl, $C_{2-5}$ alkanoyloxy-$C_{1-4}$ alkyl, aryl, aryl-$C_{1-4}$ alkyl, heteroaryl, heteroaryl-$C_{1-4}$ alkyl, or aryl, aryl-$C_{1-4}$ alkyl, heteroaryl or heteroaryl-$C_{1-4}$ alkyl substituted by at least one substituent selected from the group consisting of halogen, hydroxy, amino, nitro, cyano, $C_{1-4}$ alkyl, $C_{1-4}$ alkoxy, $C_{2-5}$ alkanoylamino, $C_{1-4}$ haloalkyl, acyloxy, $C_{2-5}$ alkoxycarbonyl and carboxyl on the aromatic ring; m is 0, 1 or 2; n is 1 or 2; the bond represented by ==== is a single bond or a double bond, and thiophene compounds of the formula:

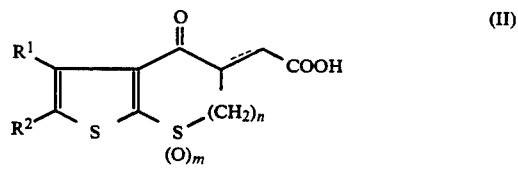

wherein each symbol is as defined above, which are synthetic intermediates of the compounds of the formula (I). The present invention also provides a pharmaceutical composition and their uses for antianxiety drugs, hypnotics, antiepileptic drugs or nootropics containing the compounds of the formula (I).

In the definitions of the above symbols and in the present specification, halogen means chlorine, bromine, fluorine or iodine; $C_{1-4}$ alkyl means alkyl having 1 to 4 carbon atoms such as methyl, ethyl, propyl, isopropyl, butyl, isobutyl or tert-butyl; $C_{1-4}$ alkoxy means alkoxy having 1 to 4 carbon atoms such as methoxy, ethoxy, propoxy, isopropoxy, butoxy, isobutoxy or tert-butoxy; acyl includes $C_{2-5}$ alkanoyl group having 2 to 5 carbon atoms such as acetyl, propionyl, butyryl, isobutyryl or pivaloyl, aralkanoyl group such as phenylacetyl, 3-phenylpropionyl or 2-phenylpropionyl, arylcarbonyl group such as benzoyl, 1-naphthoyl or 2-naphthoyl, heteroarylcarbonyl group such as nicotinoyl, isonicotinoyl, 2- or 3-thenoyl or 2- or 3-furoyl, or substituted arylcarbonyl group or substituted heteroarylcarbonyl group having at least one substituent selected from the group consisting of halogen, hydroxy, amino, nitro, cyano, $C_{1-4}$ alkyl, $C_{1-4}$ alkoxy and carboxyl on the aromatic ring; $C_{2-5}$ alkoxycarbonyl means alkoxycarbonyl having 2 to 5 carbon atoms such as methoxycarbonyl, ethoxycarbonyl, propoxycarbonyl, isopropoxycarbonyl, butoxycarbonyl, isobutoxycarbonyl or tert-butoxycarbonyl; $C_{1-4}$ alkoxy-$C_{1-4}$ alkyl means, for example, methoxymethyl, 1- or 2-methoxyethyl, 1-, 2- or 3-methoxypropyl, 1-, 2-, 3-or 4-methoxybutyl, ethoxymethyl, 1- or 2-ethoxyethyl, 1-, 2- or 3-ethoxypropyl or 1-, 2-, 3- or 4-ethoxybutyl; aryloxy-$C_{1-4}$ alkyl means phenoxymethyl, 1- or 2-phenoxyethyl, 1-, 2- or 3-phenoxypropyl, 1-, 2-, 3- or 4-phenoxybutyl, 1-naphthoxymethyl, 1-naphthoxy-1 or 2-ethyl, 1-naphthoxy-1, 2 or 3-propyl, 1-naphthoxy-1, 2, 3 or 4-butyl, 2-naphthoxymethyl, 2-naphthoxy-1 or 2-ethyl, 2-naphthoxy-1, 2 or 3-propyl or 2-naphthoxy-1, 2, 3 or 4-butyl; naphthoxy-1, 2, 3 or 4-butyl; acyloxy-$C_{1-4}$ alkyl means, for example, acetoxymethyl, propionyloxymethyl, 1- or 2-acetoxyethyl, 1- or 2-propionyloxyethyl, 3-acetoxypropyl, 3-propionyloxypropyl, benzoyloxymethyl, 2-benzoyloxyethyl, 3-benzoyloxypropyl or 4-benzoyloxybutyl; hydroxy-$C_{1-4}$ alkyl means hydroxymethyl, 1- or 2-hydroxyethyl, 1-, 2- or 3-hydroxypropyl or 1-, 2-, 3- or 4-hydroxybutyl; acyloxy-$C_{2-5}$ alkanoyl means, for example, acetoxyacetyl, 3-acetoxypropionyl, 4-acetoxybutyryl, benzoyloxyacetyl, 3-benzoyloxypropionyl or 4-benzoyloxybutyryl; $C_{1-4}$ alkoxy-$C_{2-5}$ alkanoyl means, for example, methoxyacetyl, ethoxyacetyl, propoxyacetyl, butoxyacetyl, 3-methoxypropionyl, 3-ethoxypropionyl, 3-propoxypropionyl or 3-butoxypropionyl; hydroxy-$C_{1-4}$ alkanoyl means, for example, hydroxyacetyl, 3-hydroxypropionyl or 4-hydroxybutyryl; aryloxy-$C_{2-5}$ alkanoyl means, for example, phenoxyacetyl, 3-phenoxypropionyl or 4-phenoxybutyryl; $C_{2-5}$ haloalkanoyl means alkanoyl having 2 to 5 carbon atoms substituted by halogen such as bromoacetyl, chloroacetyl, 3-bromopropionyl, 3-chloropropionyl, 4-bromobutyryl or 4-chlorobutyryl; $C_{1-8}$ alkyl means straight or branched chain alkyl having 1 to 8 carbon atoms such as methyl, ethyl, propyl, isopropyl, butyl, sec-butyl, tert-butyl, pentyl, isopentyl, neopentyl, tert-pentyl, hexyl, isohexyl, heptyl, octyl or 2-ethylhexyl; $C_{2-5}$ alkanoyloxy-$C_{1-4}$ alkyl means, for example, acetoxymethyl, 2-acetoxyethyl, 3-acetoxypropyl, 4-acetoxybutyl, propionyloxymethyl, 2-propionyloxyethyl, 3-propionyloxypropyl or 4-propionyloxybutyl; aryl means phenyl or naphthyl; aryl-$C_{1-4}$ alkyl means aralkyl having 1 to 4 carbon atoms in the alkyl moiety such as benzyl, 2-phenylethyl, 3-phenylpropyl, 4-phenylbutyl, naphthylmethyl, 2-naphthylethyl, 3-naphthylpropyl or 4-naphthylbutyl; heteroaryl means pyridyl, thienyl, furyl, pyrazolyl, imidazolyl, pyrimidinyl, pyridazinyl or benzimidazolyl; heteroaryl-$C_{1-4}$ alkyl means, for example, 2-, 3- or 4-pyridylmethyl, 2- or 3-furylmethyl or 2-or 3-thenyl; acyloxy means, for example, acetoxy, propionyloxy, butyryloxy, isobutyryloxy or benzoyloxy; $C_{1-4}$ haloalkyl means alkyl having 1 to 4 carbon atoms substituted by 1 to 3 halogens such as fluoromethyl, bromomethyl, chloromethyl, iodomethyl, difluoromethyl, trifluoromethyl, 2,2-difluoroethyl or 2,2,2-trifluoroethyl; $C_{2-5}$ alkoxycarbonyl means, for example, methoxycarbonyl, ethoxycarbonyl, propoxycarbonyl, isopropoxycarbonyl, butoxycarbonyl, isobutoxycarbonyl or tert-butoxycarbonyl; and $C_{2-5}$ alkanoylamino means, for example, acetylamino, propionylamino, butyrylamino or pivaloylamino.

The compound of the formula (I) or (II) having a chiral carbon atom can be prepared as a racemate or an optically active isomer, and the compound (I) or (II) having at least two chiral atoms can be obtained as an individual diastereomer or a mixture thereof. The present invention also embraces the mixture thereof and the individual isomers. Furthermore, the present invention embraces stereomers, too.

The compound having carboxyl group can be converted into the corresponding metallic salt thereof (e.g. sodium salt, potassium salt, magnesium salt, calcium salt or aluminum salt) by treating the compound with alkali hydroxide and so on. They are also encompassed in the scope of the invention.

Preferable compounds of the formula (I) are the compounds selected from the group consisting of 2-(4-chlorophenyl)-8-methyl-4a,5-dihydro-2H-thieno[2',3':2,3]thiopyrano[4,5-c]pyridazin-3(4H)-one, 2-(4-chlorophenyl)-9-methyl-5,6-dihydro-thieno[2',3':2,3]thiepino[4,5-c]pyridazin-3(2H)-one, 2-(4-chlorophenyl)-9-ethyl-5,6-dihydrothieno[2',3':2,3]-thiepino[4,5-c]pyridazin-3(2H)-one, 2-(4-chlorophenyl)-9-ethyl-5,6-dihydrothieno[2',3':2,3]thiepino[4,5-c]pyridazin-3(2H)-one 7-oxide, 9-bromo-2-(4-chlorophenyl)-5,6-dihydrothieno[2',3':2,3]thiepino[4,5-c]pyridazin-3(2H)-one 7-oxide, 2-(4-chlorophenyl)-9-ethyl-5,6-dihydrothieno[2',3':2,3]thiepino[4,5-c]pyridazin-3(2H)-one 7,7-dioxide, 9-ethyl-2-(4-methoxyphenyl)-5,6-dihydrothieno[2',3':2,3]thiepino[4,5-c]pyridazin-3(2H)-one, 9-ethyl-2-(4-methoxyphenyl)-5,6-dihydrothieno[2',3':2,3]thiepino[4,5-c]pyridazin-3(2H)-one 7,7-dioxide, 9-bromo-2-(4-chlorophenyl)-5,6-dihydrothieno[2',3':2,3]thiepino[4,5-c]pyridazin-3(2H)-one 7,7-dioxide, 2-(4-chlorophenyl)-9-propyl-5,6-dihydrothieno[2',3':2,3]thiepino[4,5-c]pyridazin-3(2H)-one 7-oxide and 2-(4-chlorophenyl)-9-(1-hydroxyethyl)-5,6-dihydrothieno[2',3':2,3]thiepino[4,5-c]pyridazin-3(2H)-one 7,7-dioxide.

Preferable compounds of the formula (II) are 4-oxo-5,6-dihydro-4H-thieno[2,3-b]thiopyran-5-acetic acid, 2-methyl-4-oxo-5,6-dihydro-4H-thieno[2,3-b]thiopyran-5-acetic acid, 2-bromo-4-oxo-5,6-dihydro-4H-thieno[2,3-b]thiopyran-5-acetic acid, 4-oxo-4,5,6,7-tetrahydrothieno[2,3-b]thiepin-5-acetic acid, 2-methyl-4-oxo-4,5,6,7-tetrahydrothieno[2,3-b]thiepin-5-acetic acid, 2-ethyl-4-oxo-4,5,6,7-tetrahydrothieno[2,3-b]thiepin-5-acetic acid, 2-bromo-4-oxo-4,5,6,7-tetrahydrothieno[2,3-b]thiepin-5-acetic acid, 4-oxo-2-propyl-4,5,6,7-tetrahydrothieno[2,3-b]thiepin-5-acetic acid and 2-ethyl-4-oxo-5,6-dihydro-4H-thieno[2,3-b]thiopyran-5-acetic acid.

The methods for preparing the compounds of the present invention are as follows:

Method 1

The compound of the formula (I) can be produced by subjecting a compound of the formula:

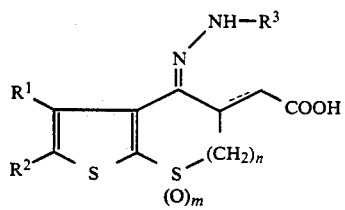 (IV)

wherein each of the symbols is as defined above, which can be obtained by reacting a compound of the formula (II) with a hydrazine derivative of the formula:

$$R^3-NHNH_2 \quad (III)$$

wherein $R^3$ is defined as above or its acid addition salt, to ring-closure reaction.

The reactions proceed by refluxing under heating in a suitable solvent, for example, an alcohol such as methanol, ethanol or propanol, or inert solvent such as benzene or toluene for 5 to 20 hours to yield the compound of the formula (I) and the compound of the formula (IV).

In case where an acid addition salt of the hydrazine derivative of the formula (III) is employed, the reaction is conducted in the presence of an acid scavenger (sodium acetate, potassium acetate, sodium hydrogencarbonate, sodium carbonate, potassium carbonate, pyridine, triethylamine, etc.).

When the compound of the formula (IV) is obtained in the above reaction, the compound of the formula (I) can be produced by refluxing the obtained compound of the formula (IV) in acetic acid for 5 to 10 hours.

The compound of the formula (I) wherein m=1 or 2, can be prepared by subjecting a compound of the formula (I) wherein m=0 to an oxidative reaction.

The reaction is carried out by keeping the reaction system at $-10°$ to $100°$ C. for 5 minutes to 10 hours in the presence of an oxidizing agent (e.g., hydrogen peroxide, peracetic acid, perbenzoic acid, m-chloroperbenzonic acid or sodium hypobromite) in a suitable solvent (inert solvent such as acetic acid, formic acid, chloroform and methylene chloride). Being kept at room temperature for 1 to 5 hours in the presence of hydrogen peroxide in acetic acid as a solvent, the compound (I) wherein m is 1 can be preferentially prepared, while when keeping the reaction system at $30°$ to $100°$ C. for 2 to 10 hours, the compound (I) wherein m is 2 can be obtained.

Method 2

The compound of the formula (I) wherein $R^3$ is $C_{1-8}$ alkyl, hydroxy-$C_{1-4}$ alkyl, $C_{2-5}$ alkanoyloxy-$C_{1-4}$ alkyl, aryl-$C_{1-4}$ alkyl, heteroaryl-$C_{1-4}$ alkyl, or aryl-$C_{1-4}$ alkyl, heteroaryl-$C_{1-4}$ alkyl having substituent(s) on the aromatic ring, can be prepared by reacting the compound of the formula (I) wherein $R^3$ is hydrogen, with a compound of the formula $$R^4-X^1 \quad (V)$$

wherein $R^4$ is $C_{1-8}$ alkyl, hydroxy-$C_{1-8}$ alkyl, $C_{2-5}$ alkanoyloxy-$C_{1-4}$ alkyl, heteroaryl-$C_{1-4}$ alkyl having substituent(s) on the aromatic ring, and $X^1$ is a reactive atom or group (e.g., halogen such as chlorine or bromine, or methanesulfonyloxy, toluenesulfonyloxy or benzenesulfonyloxy).

The reaction is carried out by keeping at $0°$ to $50°$ C. for 1 to 10 hours in the presence of an acid scavenger (e.g., sodium hydride, sodium amide, sodium methoxide, sodium ethoxide, potassium hydroxide or sodium hydroxide) in a suitable solvent such as nonpolar solvent (e.g., benzene, toluene or xylene), or polar solvent (e.g., N,N-dimethylformamide or acetonitrile).

Method 3

The compound of the formula (I) wherein the bond ===== is a double bond can be synthesized also by adding bromine in an amount of 1-1.5 times mol dropwise to the corresponding compound of the formula (I) wherein said bond is a single bond in acetic acid as the solvent at $20°-60°$ C. [Journal of Medicinal Chemistry, vol. 14, 262 (1971)] or by reacting the compound of the formula (I) wherein the bond is a single bond with sodium-m-nitrobenzenesulfonate (Bachmann method. The specification of United Kingdom Patent No. 1168291).

Alternatively, the compound of the formula (I) wherein the bond ==== is a double bond can be prepared by reacting the compound of the formula (I) wherein said bond is a single bond with a suitable acid (e.g. hydrohalogenic acid such as hydrobromic acid, hydrochloric acid or hydriodic acid, alkyl sulfonic acid such as methanesulfonic acid or trifluoromethanesulfonic acid, aliphatic carboxylic acid such as acetic acid, formic acid or trifluoroacetic acid, aryl sulfonic acid such as p-toluenesulfonic acid, or the mixture thereof), if necessary in the presence of sulfoxide (e.g. dimethyl sulfoxide, diphenyl sulfoxide, phenyl vinyl sulfoxide, dibenzyl sulfoxide, p-tolyl sulfoxide, methyl phenyl sulfoxide or resorcinol sulfoxide), at $0°$ C. to the boiling point of the acid employed for 30 minutes to 30 hours.

Method 4

The compound of the formula (I) wherein $R^2$ is acyl, $C_{1-4}$ alkoxy-$C_{2-5}$ alkanoyl, aryloxy-$C_{2-5}$ alkanoyl or $C_{2-5}$ halo-alkanoyl can be prepared by reacting the compound of the formula:

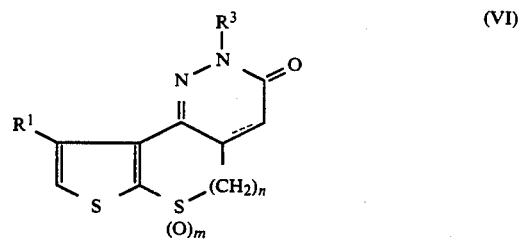 (VI)

wherein each symbol is as defined above, with a compound of the formula:

$$R^5COOH \quad (VII)$$

wherein $R^5$ is $C_{1-4}$ alkyl, $C_{1-4}$ haloalkyl, $C_{1-4}$ alkoxy-$C_{1-4}$ alkyl, aryloxy-$C_{1-4}$ alkyl, aryl, aryl-$C_{1-4}$ alkyl or heteroaryl, or a reactive derivative (e.g. acid halide or acide anhydride).

In case where a free carboxylic acid compound of the formula (VII) is employed, the reaction is conducted in the presence of dehydrating agent (e.g. polyphosphoric acid) at room temperature to $150°$ C.

In case where an acid halide as the reactive derivative of the formula (VII) is employed, the reaction is carried out in the presence of Lewis acid (e.g. alminium chloride, tin chloride or iron chloride) in a suitable inert solvent (e.g. benzene, toluene, chloroform, methylene chloride or dichloroethane) at −10° C. to 100° C. for 5 minutes to 20 hours.

Method 5

The compound of the formula:

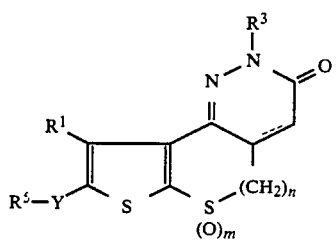
(IX)

wherein Y is —CH(OH)— or —CH₂— and other symbols are as defined above, can be produced by reducing the compound of the formula:

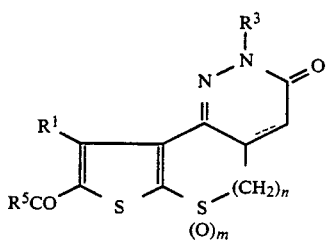
(VIII)

wherein each symbol is as defined above, obtained in the above method 4, with reducing agent such as sodium boron hydride, lithium aluminum boron hydride or triethylsilane in a suitable solvent (e.g. methanol, ethanol, propanol, butanol or acetic acid), or by catalytic reduction in the presence of palladium, rhodium or platinum at −10° to 150° C. for 5 minutes to 20 hours.

Method 6

The haloalkanoyl compound of the formula:

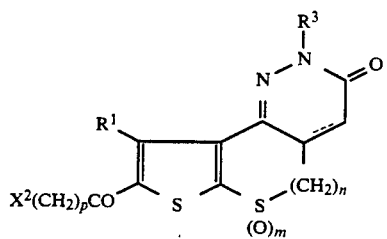
(X)

wherein $X^2$ is halogen, p is 1 to 3 and other symbols are as defined above, obtained in the above Method 4, is reacted with a metal salt (e.g. sodium, potassium or lithium) of carboxylic acid of the formula:

$R^6COOH$    (XI)

wherein $R^6$ is $C_{1-4}$ alkyl, aryl, aryl-$C_{1-4}$ alkyl or heteroaryl, to produce a compound of the formula:

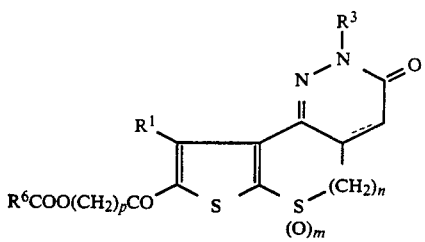
(XII)

wherein each symbol is as defined above.

The reaction proceeds in a suitable solvent (e.g. inert solvent such as acetic acid, chloroform, methylene chloride, benzene, toluene or N,N-dimethylformamide) at room temperature to 150° C. for 1 to 20 hours.

Method 7

The compound of the formula (X) is reacted with a metal salt (e.g. sodium, potassium or lithium) of alcoholic compound of the formula:

$R^6OH$    (XIII)

wherein $R^6$ is as defined above, to produce a compound of the formula:

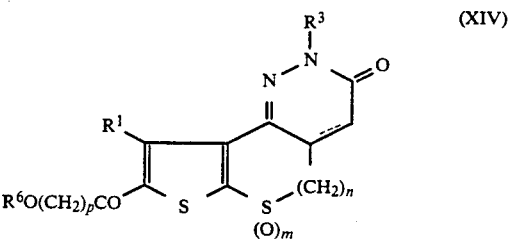
(XIV)

wherein each symbol is as defined above.

The reaction proceeds in a suitable solvent (e.g. inert solvent such as methanol, ethanol, tetrahydrofuran, benzene, toluene or N,N-dimethylformamide) at room temperature to 150° for 1 to 20 hours.

Method 8

The compound of the formula:

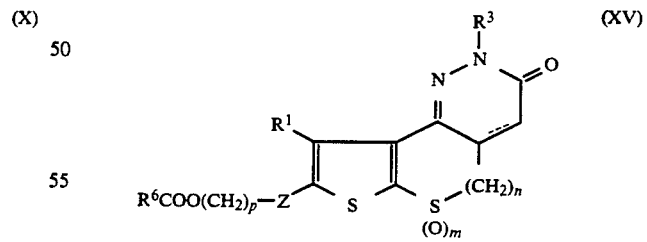
(XV)

wherein Z is —CH₂—, —CH(OH)— or —CO— and other symbols are as defined above, is subjected to hydrolysis in the presence of a solution of acid (e.g. hydrochloric acid, sulfuric acid, phosphoric acid or nitric acid) or alkali (e.g. sodium hydroxide, potassium hydroxide, lithium hydroxide, barium hydroxide or potassium carbonate) in a suitable solvent (inert solvent such as acetic acid, methanol, ethanol, butanol or water) at −10° to 150° C. for 1 to 20 hours to produce a compound of the formula:

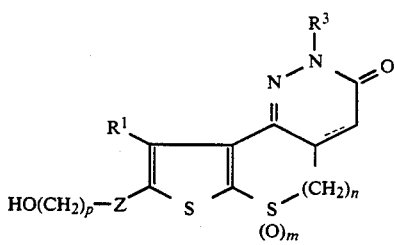

wherein each symbol is as defined above.

Method 9

The compound of the formula (XVI) is reacted with a compound of the formula $$R^7X^2 \qquad (XVII)$$

wherein $R^7$ is $C_{1-4}$ alkyl or aryl-$C_{1-4}$ alkyl and $X^2$ is halogen, in a suitable solvent (inert solvent such as methanol, ethanol, propanol, butanol, N,N-dimethylformamide, tetrahydrofuran, benzene or toluene in the presence of an acid scavenger (e.g. sodium hydride, sodium amide, sodium methoxide, sodium ethoxide, potassium hydroxide or sodium hydroxide) at room temperature to 150° C. for 1 to 20 hours to produce a compound of the formula:

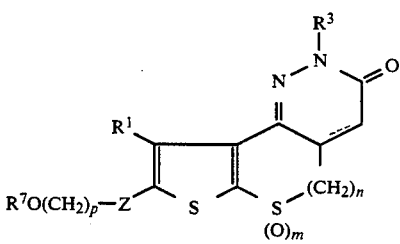

wherein each symbol is as defined above.

The methods for preparing the compounds of the formula (II) are as follows:

Method 10

The compound of the formula (II) can be produced by converting the corresponding compound of the formula:

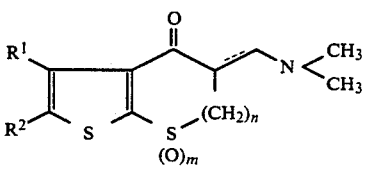

wherein each symbol is as defined above, or acid addition salt thereof to their quaternary ammonium compounds by adding methyl iodide thereto in acetone and retaining the mixture at room temperature for 2 to 5 hours, followed by converting the quaternary ammonium compounds to the corresponding cyano compounds of the formula:

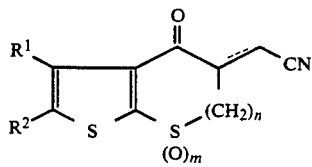

wherein each symbol is as defined above, by adding potassium cyanide or sodium cyanide thereto in an aqueous methanol and reacting the mixture at 30° to 50° C. for 4 to 10 hours, followed by adding the thus-obtained compound of the formula (XX) to acetic acid and conc. hydrochloric acid and refluxing the mixture under heating for 2 to 5 hours.

The compound of the formula (XIX) wherein the bond represented by === is a single bond, can be prepared by subjecting the compound of the formula:

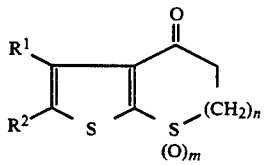

wherein each symbol is as defined above, to Mannich reaction. On the other hand, the compound of the formula (XIX) wherein said bond is a double bond can be prepared by reacting the compound of the formula (XXI) with N,N-dimethylformamide dimethyl acetal.

Method 11

The compound of the formula:

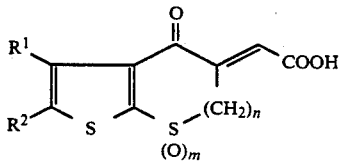

wherein each symbol is as defined above, can be prepared by, for example, reacting the compound of the formula (XXI) with glyoxylic acid in ethanol with stirring under ice-cooling in the presence of a base (e.g. sodium hydroxide solution) for 2 hours and further stirring the mixture at room temperature to 50° C. for 1 to 5 hours.

The compound of the formula:

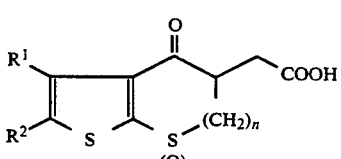

wherein each symbol is as defined above, can be obtained by subjecting the compound of the formula (II-1) to reduction reaction in the presence of reducing agent (e.g. sodium boronhydride, lithium aluminum hydride or zinc) in an alcoholic solvent (e.g. methanol) with stirring at room temperature for 1 to several hours.

Method 12

The compound of the formula (XXI) is refluxed overnight in toluene in the presence of p-toluenesulfonic acid, and the resulting compound of the formula:

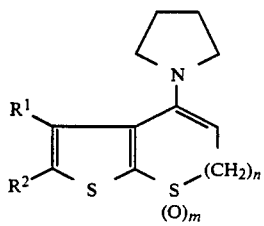
(XXII)

wherein each symbol is as defined above, is refluxed at room temperature or the refluxing temperature is benzene for 1 to several hours in the presence of, for example, ethyl bromoacetate, and the thus obtained ester compound of the formula:

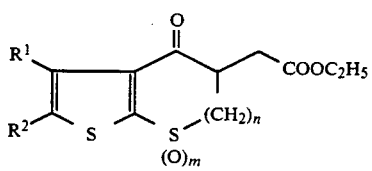
(XXIII)

wherein each symbol is as defined above, is subjected to hydrolysis to produce the compound of the formula (II-2).

Method 13

The compound of the formula (XXI) is reacted with, for example, diethyl carbonate in the presence of sodium hydride, the resulting compound of the formula:

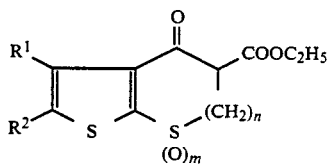
(XXIV)

wherein each symbol is as defined above, is reacted with, for example, ethyl bromoacetate in the presence of a suitable base such as potassium carbonate, and the thus obtained compound of the formula:

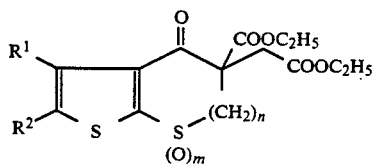
(XXV)

wherein each symbol is as defined above, is subjected to hydrolysis to produce the compound of the formula (II-2).

The compound of the formula (II) wherein m=1 or 2, i.e., oxide or dioxide compound can be prepared by subjecting the corresponding compound of the formula (II) wherein m is 0 to an oxidative reaction.

The compounds of the present invention which can be produced in the above-mentioned manner can be isolated and purified by a conventional method such as column chromatography or recrystallization.

When the obtained product is a racemate, it can be separated into desired optically active isomers by means of a fractional recrystallization of a salt with an optically active acid, or by column chromatography filled with an optically active carrier. Individual diastereomers can be separated by the method such as fractional crystallization or chromatography. Such compounds can also be obtained by using an optically active starting material. Furthermore, the stereoisomers can be isolated by the method such as recrystallization or column chromatography.

The compounds of the formula (I) exhibit high affinities (Ki values are $10^{-9}-10^{-10}$M) for benzodiazepine (BZP) receptors and have an antagonistic action against chemical convulsants such as bicuculline and pentylenetetrazole. They also possess an inhibitory action against amnesia induced by electroconvulsive shock. Furthermore, they have antiepileptic action since an inhibitory action against the maximum electro-shock has been recognized.

The pharmacological actions of the compounds in the present invention are shown with the experimental methods therefor below.

EXPERIMENT 1

Displacement ability for Benzodiazepine receptors $^3$H-DZP binding assay was carried out according to the previously described method in Life Science, vol. 20, 2101 (1977).

The crude cynaptosomal fraction prepared from the cerebral cortex of Wistar rats aged 9–10 weeks was suspended in 50 mM Tris-hydrochloric acid buffer (pH 7.4) containing 120 mM sodium chloride and 5 mM potassium chloride. These suspensions were used for the following experiment.

The reaction was started by the addition of synaptosomal suspension to the solution containing tritiated diazepam (final concentration is 2 nM) and a known concentration of test compounds at 0° C. for 20 min. The binding was stopped by the filtration under vacuum through Whatman GF/B filters and the filters were immediately washed with the above-mentioned buffer. The radioactivity on the filters was measured by a liquid scintillation counter.

The binding affinities of the compound of the present invention for benzodiazepine receptors are evaluated from its displacement ability for tritiated diazepam at its binding site, which is represented as Ki value (nM).

The results of the experiment are shown in Table 1.

EXPERIMENT 2

Anti-Bicuculline Action

The anti-bicuculline action of the test compounds was done according to the method reported in Life Science, vol. 21, 1779 (1977).

The test was carried out using groups of 7–14 male ddY mice weighing 20–25 g. The animals were challenged with (+) bicuculline (0.6 mg/kg i.v.) 1 hour after the oral administration of the test compounds. The ED$_{50}$ values were calculated by the probit method as the dose which prevent the tonic extention in half of the animals.

The results of the experiment are shown in Table 1.

TABLE 1

| Test compound (Example No.) | Affinity for BZP receptors $K_i$ (nM) | Antibicuculline effect $ED_{50}$ (mg/kg, p.o.) |
|---|---|---|
| 22 | 1.8 | 0.49 |
| 25 | 1.4 | 0.66 |
| 26 | 1.4 | 0.56 |
| 28 | 0.63 | 0.23 |
| 50 | 0.97 | 0.87 |
| 58 | 0.56 | 0.4 |
| 64 | 0.44 | 1.4 |
| 65 | 0.12 | 1.4 |
| 70 | 0.62 | 0.62 |

EXPERIMENT 3

Antianxiety effect (Vogel type conflict test)

The experimental procedure used modified the method of Vogel et al (1971). Wistar rats were used. They were deprived of water for 72 hr before the test. The rats were placed in a plexiglas conflict test box (light compartment: 38×38×20 cm, dark compartment: 10×10×20 cm). A water bottle with a stainless steel spout was fitted to the middle of the outside, so that the spout extended 3 cm into the box at a height of 10 cm above the grid floor. A drinkometer circuit (Ohara Inc. Nihon Koden) was connected with the spout and the number of licks were counted with the spout and the number of licks were counted. The rat was placed into the apparatus where an electric shock (0.2–0.3 mA, 0.3 sec) was given one every 20th lick. After the rat received the first electric shock, the number of shocks were recorded during the subsequent 3 min test period. The test compounds were administered orally 1 hr before the test. The minimum effective dose (MED) was defined as the lowest dose producing a statistically significant difference between 0.5% MC-treated (control) and test drug treated punished responses (One-way ANOVA test; $P<0.05$).

The results are shown in Table 2.

TABLE 2

| Test compound (Example No.) | Antianxiety effect MED (mg/kg, p.o.) |
|---|---|
| 28 | 2.5 |

EXPERIMENT 4

Effects on seizure induced by maximal electro-shock (anti-MES action)

The test was carried out using groups of five male ddY mice. The animals were challenged with a maximal electroshock (MES. AC 2000 V, 12.5 mA, 0.2 sec) delivered through bilatesal corneal electrodes 1 hour after the oral or intraperitoneal administration of the test compounds. Antagonism of MES-induced seizure was defined as the absence of the tonic extention.

The results are shown in Table 3.

TABLE 3

| Test compound (Example No.) | Dose (mg/kg) | Inhibitory rate (%) |
|---|---|---|
| 14 | 30 (i.p.) | 100 |
| 14 | 30 (p.o.) | 40 |
| 14 | 100 (p.o.) | 100 |
| 25 | 30 (i.p.) | 80 |
| 69 | 30 (i.p.) | 80 |
| 71 | 30 (i.p.) | 100 |

EXPERIMENT 5

MUSCLE-relaxant effect

Groups of 10 male ddY mice were used. The mice were gently placed on the rod (2.8 cm in diameter rotating at 11 r.p.m.) 1 hour after the oral administration of the test compounds. The $ED_{50}$ value was calculated by the probit method as the dose which caused 50% of the animals to drop from the rotarod within 1 minute.

EXPERIMENT 6

Effect on electroconvulsive shock-induced amnesia

Twenty male ddY mice were used per each group to investigate the action of the test compounds on learning and memory ability of amnesia-induced mice by observing a stepthrough passive avoidance response. Amnesia-induced animals were prepared by applying electroconvulsive shock (ECS) immediately after the acquisition trial and the retention test was carried out 24 hours after the acquisition trial. Test compounds were administered intraperitoneally (i.p.) before the acquisition trial.

EXPERIMENT 7

Acute toxicity

Groups of five male ddY mice were used. The mice were administered with 300 mg/kg of the compound of Example 22 intraperitoneally, but all mice survived for 5 days after the administration. Similarly, the mice were orally administered with 1000 mg/kg of the compound, but they survived for 5 days after the administration.

As apparent from the foregoing various pharmacological studies including experiments, the compounds (I) of the present invention have a high affinity of $10^{-9}$–$10^{-10}$M for BZP receptors and exhibit an antagonistic action against chemical convulsion-inducing agents such as bicuculline and pentylenetetrazole and further strong antianxiety effect in conflict test, whereas they influence to a small extent on somatic functions such as muscle-relaxing actions. Thus, they are useful as selective antianxiety drugs. Also, they exhibit anti-MES action and useful as antiepileptic drugs. Furthermore, since they possess an inhibitory action an amnesia induced by electroconvulsive shock, they are useful nootropics such as amnesia-treating drugs, brain function-activating drugs and antidementiac drugs. They are also of value as hypnotics or antidotes for excessive administration of or toxicosis by existent antianxiety drugs such as diazepam. Besides, the compounds of the formula (II) are useful as the synthetic intermediates therefor.

When the compounds of the formula (I) are used as pharmaceutically, a therapeutically effective amount of the compounds and adequate pharmacologically acceptable additives such as excipient, carrier, diluent and so on are mixed to be formulated into a form such as tablets, capsules, granules, syrups, injectable solutions, suppositories, dispersible powders or the like and are administered in a form mentioned above. The dosage, for example, in the case of oral administration, is generally about 5–500 mg daily per adult, which is once a day or in divided doses several times a day administered.

Formulation Example

The tablets containing 10 mg of the compound (I) of the present invention can be prepared by the following composition

| Compound (I) | 10.0 mg |
| --- | --- |
| Lactose | 58.5 mg |
| Corn starch | 25.0 mg |
| Crystalline cellulose | 20.0 mg |
| Polyvinyl pyrrolidine K-30 | 2.0 mg |
| Talc | 4.0 mg |
| Magnesium stearate | 0.5 mg |
| | 120.0 mg |

Compound (I) is crushed with an atomizer to make a fine powder having an average particle size below 10 μ. The fine powder of Compound (I), lactose, corn starch and crystalline cellulose are mixed well in a kneader and then kneaded with a binder prepared by polyvinyl pyrrolidone. The wet mass is passed through a 200 mesh sieve and then dried in an oven at 50° C. The dry granule containing 3–4% of water content is forced through a 24 mesh sieve. Talc and magnesium stearate are mixed and compressed into tablets by using a rotary tableting machine with a flat punch of 8 mm diameter.

The present invention will be explained by the following examples in more detail, but these examples are not to be construed as limiting the present invention.

REFERENCE EXAMPLE 1

A mixture of 18 g of dimethylamine hydrochloride and 18 g of 37% formalin is stirred for 30 minutes and the temperature of the mixture is raised to 70° C. To the mixture is added 80 ml of acetic anhydride dropwise for 20 minutes at 70°–80° C. and kept for about 20 minutes at the same temperature. To the mixture is added 32.6 g of 5,6-dihydro-4H-thieno[2,3-b]thiopyran-4-one. The mixture is kept for 4 hours at the same temperature and then the solvent is distilled off under reduced pressure. To the residue is added acetone, and the precipitated crystals are collected by filtration and recrystallized from a mixed solvent of ethanol and isopropyl ether to give 35 g of 5-dimethylaminomethyl-5,6-dihydro-4H-thieno[2,3-b]thiopyran-4-one hydrochloride as white crystals, melting at 163°–166° C.

The following compounds can be prepared in a similar manner as the above Reference example 1.

REFERENCE EXAMPLE 2

2-Methyl-5-dimethylaminomethyl-5,6-dihydro-4H-thieno[2,3-b]thiopyran-4-one hydrochloride, melting at 164°–166° C.

REFERENCE EXAMPLE 3

2-Methyl-5-dimethylaminomethyl-4,5,6,7-tetrahydrothieno[2,3-b]thiepin-4-one hydrochloride, melting at 182°–183° C.

REFERENCE EXAMPLE 4

2-Ethyl-5-dimethylaminomethyl-4,5,6,7-tetrahydrothieno[2,3-b]thiepin-4-one hydrochloride, melting at 176°–179° C.

REFERENCE EXAMPLE 5

To a solution of 10 g of 2-methyl-5-dimethylaminomethyl-4,5,6,7-tetrahydrothieno[2,3-b]thiepin-4-one hydrochloride in 50 ml of water is added 3 ml of 28% aqueous ammonia. After the mixture is extracted with chloroform, the extract is washed with water, dried over magnesium sulfate and then the chloroform is distilled off. The resulting residue is dissolved in 100 ml of acetone and to the acetone solution is added 2.3 ml of methyl iodide. The precipitated crystals are collected by filtration and recrystallized from aqueous ethanol to give 12.4 g of N,N,N-trimethyl-N-[(2-methyl-4-oxo-4,5,6,7-tetrahydrothieno[2,3-b]thiepin-5-yl)methyl]ammonium iodide as white crystals, melting at 193°–194° C.

The following compounds can be prepared in a similar manner as the above Reference example 5.

REFERENCE EXAMPLE 6

N,N,N-Trimethyl-N-[(4-oxo-4,5,6,7-tetrahydrothieno[2,3-b]thiepin-5-yl)methyl]ammonium iodide, melting at 190°–192°.

REFERENCE EXAMPLE 7

N,N,N-Trimethyl-N-[(2-ethyl-4-oxo-4,5,6,7-tetrahydrothieno[2,3-b]thiepin-5-yl)methyl]ammonium iodide, melting at 181°–182° C.

REFERENCE EXAMPLE 8

To a solution of 25.3 g of potassium cyanide in 100 ml of water is added 400 ml of methanol and to the solution is added 41 g of 5-dimethylaminomethyl-5,6-dihydro-4H-thieno[2,3-b]thiopyran-4-one hydrochloride with stirring. The mixture is stirred for 3 hours at 45°–50° C. and then concentrated under reduced pressure. To the residue is added water and the mixture is extracted with chloroform. The extract is washed with water, dried over magnesium sulfate and the chloroform is distilled off. The residue is subjected to chromatography on silica gel and eluted with chloroform to give 28 g of 4-oxo-5,6-dihydro-4H-thieno[2,3-b]thiopyran-5-acetonitrile as pale brown oil.

The following compound can be prepared in a similar manner as the above Reference example 8.

REFERENCE EXAMPLE 9

2-Methyl-4-oxo-5,6-dihydro-4H-thieno[2,3-b]thiopyran-5-acetonitrile, melting at 94°–95.5° C.

REFERENCE EXAMPLE 10

To a suspension of 59.5 g of N,N,N-trimethyl-N-[(4-oxo-4,5,6,7-tetrahydrothieno[2,3-b]thiepin-5-yl)methyl]ammonium iodide in 400 ml of methanol is added a solution of 25.2 g of potassium cyanide in 100 ml of water with stirring at room temperature. The mixture is stirred for 1.5 hours at the same temperature, poured into 500 ml of water and then extracted with chloroform. The extract is washed with water, dried over magnesium sulfate and the chloroform is distilled off. The resulting crystals are recrystallized from ethanol to give 32 g of 4-oxo-4,5,6,7-tetrahydrothieno[2,3-b]thiepin-5-acetonitrile as white crystals, melting at 68°–70° C.

The following compounds can be prepared in a similar manner as the above Reference example 10.

REFERENCE EXAMPLE 11

2-Methyl-4-oxo-4,5,6,7-tetrahydrothieno[2,3-b]thiepin-5-acetonitrile, melting at 102°–103° C.

REFERENCE EXAMPLE 12

2-Ethyl-4-oxo-4,5,6,7-tetrahydrothieno[2,3-b]thiepin-5-acetonitrile, melting at 84°–86° C.

EXAMPLE 1

To a solution of 25 g of 4-oxo-5,6-dihydro-4H-thieno[2,3-b]thiopyran-5-acetonitrile in 100 ml of acetic acid is added 50 ml of concentrated hydrochloric acid and the mixture is refluxed under heating for 2 hours. Then, the mixture is poured into 500 ml of ice-cold water. The precipitated crystals are collected by filtration, washed with water and recrystallized from a mixed solvent of toluene and isopropyl ether to give 16.5 g of 4-oxo-5,6-dihydro-4H-thieno[2,3-b]thiopyran-5-acetic acid as white crystals, melting at 124°–127° C.

The following compounds can be prepared in a similar manner as the above Example 1.

EXAMPLE 2

2-Methyl-4-oxo-5,6-dihydro-4H-thieno[2,3-b]thiopyran-5-acetic acid, melting at 133°–135° C.

EXAMPLE 3

2-Bromo-4-oxo-5,6-dihydro-4H-thieno[2,3-b]thiopyran-5-acetic acid, melting at 158°–160° C.

EXAMPLE 4

4-Oxo-4,5,6,7-tetrahydrothieno[2,3-b]thiepin-5-acetic acid, melting at 151°–152° C.

EXAMPLE 5

2-Methyl-4-oxo-4,5,6,7-tetrahydrothieno[2,3-b]thiepin-5-acetic acid, melting at 183°–186° C.

EXAMPLE 6

2-Ethyl-4-oxo-4,5,6,7-tetrahydrothieno[2,3-b]thiepin-5-acetic acid, melting at 180°–182° C.

EXAMPLE 7

2-Bromo-4-oxo-4,5,6,7-tetrahydrothieno[2,3-b]thiepin-5-acetic acid, melting at 164°–166° C.

EXAMPLE 8

4-Oxo-2-propyl-4,5,6,7-tetrahydrothieno[2,3-b]thiepin-5-acetic acid, melting at 177°–179° C.

EXAMPLE 9

2-Ethyl-4-oxo-5,6-dihydro-4H-thieno[2,3-b]thiopyran-5-acetic acid, melting at 102°–104° C.

EXAMPLE 10

A mixture of 4.0 g of 4-oxo-5,6-dihydro-4H-thieno[2,3-b]thiopyran-5-acetic acid and 3.3 g of 4-chlorophenylhydrazine in 70 ml of ethanol is refluxed under heating for 6.5 hours. After cooling, the reaction mixture is concentrated under reduced pressure. The residue is dissolved in 50 ml of acetic acid and the solution is refluxed under heating for 2 hours. Then, the resultant mixture is concentrated under reduced pressure, the residue is subjected to chromatography on silica gel and eluted with chloroform. The crystals obtained from the fraction are recrystallized from a mixed solvent of chloroform and ethanol to give 4.3 g of 2-(4-chlorophenyl)-4a,5-dihydro-2H-thieno[2',3':2,3]thiopyrano[4,5-c]pyridazin-3(4H)-one as pale brown crystals, melting at 162°–164° C.

EXAMPLE 11

A mixture of 2.4 g of 2-bromo-4-oxo-5,6-dihydro-4H-thieno[2,3-b]thiopyran-5-acetic acid and 1.3 g of 4-chlorophenylhydrazine in 40 ml of ethanol is refluxed under heating for 14 hours. After cooling, the precipitated crystals are collected by filtration, washed with ethanol and then recrystallized from a mixed solvent of chloroform and ethanol to give 1.3 g of 8-bromo-2-(4-chlorophenyl)-4a,5-dihydro-2H-thieno[2',3':2,3]thiopyrano[4,5-c]pyridazin-3(4H)-one as pale brown crystals, melting at 169°–170° C.

EXAMPLE 12

A mixture of 3.0 g of 2-methyl-4-oxo-5,6-dihydro-4H-thieno[2,3-b]thiopyran-5-acetic acid and 2.0 g of 4-chlorophenylhydrazine in 50 ml of ethanol is refluxed under heating for 9 hours. After cooling, the mixture is concentrated under reduced pressure, the residue is subjected to column chromatography on silica gel and eluted with chloroform. The crystals obtained from the fraction are recrystallized from a mixed solvent of chloroform and ethanol to give 2.0 g of 2-(4-chlorophenyl)-8-methyl-4a,5-dihydro-2H-thieno[2',3':2,3]thiopyrano[4,5-c]pyridazin-3(4H)-one as pale brown crystals, melting at 142°–144° C.

EXAMPLE 13

The reaction and procedure are conducted in the same manner as in Example 12 using methyl 3-hydrazino-5-methylthiophene-2-carboxylate in place of 4-chlorophenylhydrazine as used in Example 12 to give 2-(2-methoxycarbonyl-5-methyl-3-thienyl)-8-methyl-4a,5-dihydro-2H-thieno[2',3':2,3]thiopyrano[4,5-c]pyridazin-3(4H)-one, melting at 164°–166° C.

EXAMPLE 14

A mixture of 3.7 g of 4-oxo-4,5,6,7-tetrahydrothieno[2,3-b]thiepin-5-acetic acid and 2.6 g of 4-chlorophenylhydrazine in 50 ml of ethanol is refluxed under heating for 6.5 hours. Then, the reaction mixture is concentrated under reduced pressure. The resulting residue is dissolved in 40 ml of acetic acid and the mixture is further refluxed under heating for 1.5 hours. After cooling, the mixture is concentrated under reduced pressure, and the residue is subjected to column chromatography on silica gel and eluted with chloroform. The crystals obtained from the fraction are recrystallized from a mixed solvent of chloroform and ethanol to give 1.7 g of 2-(4-chlorophenyl)-4,4a, 5,6-tetrahydrothieno[2',3':2,3]thiopyrano[4,5-c]pyridazin-3(2H)-one as pale brown crystals, melting at 134°–135° C.

The following compounds can be prepared in a similar manner as the above Example 14.

EXAMPLE 15

2-(4-Chlorophenyl)-9-methyl-4,4a,5,6-tetrahydrothieno-[2',3':2,3]thiepino[4,5-c]pyridazin-3(2H)-one, melting at 153°–154° C.

EXAMPLE 16

9-Methyl-2-(4-methylphenyl)-4,4a,5,6-tetrahydrothieno-[2',3':2,3]thiepino[4,5-c]pyridazin-3(2H)-one, melting at 131°–132° C.

EXAMPLE 17

9-Methyl-2-phenyl-4,4a,5,6-tetrahydrothieno[2',3':2,3]thiepino[4,5-c]pyridazin-3(2H)-one, melting at 144°–146° C.

EXAMPLE 18

2-(6-Chloro-2-pyridyl)-9-methyl-4,4a,5,6-tetrahydrothieno[2',3':2,3]thiepino[4,5-c]pyridazin-3(2H)-one, melting at 155°–157° C.

EXAMPLE 19

9-Bromo-2-(4-chlorophenyl)-4,4a,5,6-tetrahydrothieno-[2',3':2,3]thiepino[4,5-c]pyridazin-3(2H)-one, melting at 121°–123° C.

EXAMPLE 20

2-(4-Chlorophenyl)-9-ethyl-4,4a,5,6-tetrahydrothieno-[2',3':2,3]thiepino[4,5-c]pyridazin-3(2H)-one, melting at 101°–104° C.

EXAMPLE 21

To a solution of 3.6 g of 2-(4-chlorophenyl)-9-methyl-4,4a,5,6-tetrahydrothieno[2',3':2,3]thiepino[4,5-c]pyridazin-3(2H)-one in 50 ml of acetic acid is added dropwise a solution of 1.7 g of bromine in 15 ml of acetic acid stirring for 15 minutes at 40°–45° C. The mixture is stirred for 20 minutes at the same temperature and then poured into 200 ml of water. The precipitated crystals are collected by filtration and washed with water. The resulting crystals are subjected to column chromatography on silica gel and eluted with chloroform. The crystals obtained from the fraction are recrystallized from a mixed solvent of chloroform and ethanol to give 2.2 g of 2-(4-chlorophenyl)-9-methyl-5,6-dihydrothienol[2',3':2,3]thiepino[4,5-c]pyridazin-3(2H)-one as pale brown crystals, melting at 150°–151° C.

EXAMPLE 22

The reaction and procedure are conducted in the same manner as in Example 21 using 2-(4-chlorophenyl)-9-ethyl-4,4a,5,6-tetrahydrothieno[2',3':2,3]-thiepino[4,5-c]pyridazin-3(2H)-one in place of 2-(4-chlorophenyl)-9-methyl-4,4a,5,6-tetrahydrothieno[2',3':2,3]thiepino[4,5-c]pyridazin-3(2H)-one as used in Example 21 to give 2-(4-chlorophenyl)-9-ethyl-5,6-dihydrothieno[2',3':2,3]thiepino[4,5-c]pyridazin-3(2H)-one, melting at 127°–128° C.

EXAMPLE 23

The reaction and procedure are conducted in the same manner as in Example 21 using 9-bromo-2-(4-chlorophenyl)-4,4a,5,6-tetrahydrothieno[2',3':2,3]-thiepino[4,5-c]pyridazin-3(2H)-one in place of 2-(4-chlorophenyl)-9-methyl-4,4a,5,6-tetrahydrothieno[2',3':2,3]thiepino[4,5-c]pyridazin-3(2H)-one as used in Example 21 to give 9-bromo-2-(4-chlorophenyl)-5,6-dihydrothieno[2',3':2,3]thiepino[4,5-c]pyridazin-3(2H)-one, melting at 148°–151° C.

EXAMPLE 24

To a solution of 1.0 g of 2-(4-chlorophenyl)-9-methyl-5,6-dihydrothieno[2',3':2,3]thiepino[4,5-c]pyridazin-3(2H)-one in 50 ml of formic acid is added 0.3 ml of 35% aqueous hydrogen peroxide solution with stirring at 5° C. and the mixture is stirred for 10 minutes at the same temperature. To the mixture is further added 0.3 ml of aqueous hydrogen peroxide solution and the mixture is stirred for 20 minutes. Then, the mixture is poured into water, extracted with chloroform three times and the extract is washed with water and dried over magnesium sulfate. After the chloroform is distilled off under reduced pressure, the resulting crystals are recrystallized from a mixed solvent of chloroform and ethanol to give 1.0 g of 2-(4-chlorophenyl)-9-methyl-5,6-dihydrothieno[2',3':2,3]thiepino[4,5-c]pyridazin-3(2H)-one 7-oxide as white crystals, melting at 174°–175° C. with decomposition.

EXAMPLE 25

The reaction and procedure are conducted in the same manner as in Example 24 using 2-(4-chlorophenyl)-9-ethyl-5,6-dihydrothieno[2',3':2,3]-thiepino[4,5-c]pyridazin-3(2H)-one in place of 2-(4-chlorophenyl)-9-methyl-5,6-dihydrothieno[2',3':2,3]-thiepino[4,5-c]pyridazin-3(2H)-one as used in Example 24 to give 2-(4-chlorophenyl)-9-ethyl-5,6-dihydrothieno[2',3':2,3]thiepino[4,5-c]pyridazin-3(2H)-one 7-oxide, melting at 173°–174° C. with decomposition.

EXAMPLE 26

The reaction and procedure are conducted in the same manner as in Example 24 using 9-bromo-2-(4-chlorophenyl)-5,6-dihydrothieno[2',3':2,3]thiepino[4,5-c]pyridazin-3(2H)-one in place of 2-(4-chlorophenyl)-9-methyl-5,6-dihydrothieno[2',3':2,3]thiepino[4,5-c]pyridazin-3(2H)-one as used in Example 24 to give 9-bromo-2-(4-chlorophenyl)-5,6-dihydrothieno[2',3':2,3]thiepino[4,5-c]pyridazin-3(2H)-one 7-oxide, melting at 184°–185° C. with decomposition.

EXAMPLE 27

To a solution of 0.9 g of 2-(4-methoxyphenyl)-9-methyl-4,4a,5,6-tetrahydrothieno[2',3':2,3]thiepino[4,5-c]pyridazin-3(2H)-one in 10 ml of formic acid is added 1.0 ml of 35% aqueous hydrogen peroxide solution with stirring at room temperature and the mixture is stirred for 3 hours at the same temperature, and then water is added thereto. The mixture is extracted with chloroform three times, and the extract is washed with water and dried over magnesium sulfate. The chloroform is distilled off, the resulting crystals are recrystallized from a mixed solvent of chloroform and ethanol to give 2-(4-methoxyphenyl)-9-methyl-4,4a,5,6-tetrahydrothieno[2',3':2,3]thiepino[4,5-c]pyridazin-3(2H)-one 7,7-dioxide as white crystals, melting at 190°–191° C.

The following compounds can be prepared in a similar manner as the above examples.

EXAMPLE 28

2-(4-Chlorophenyl)-9-ethyl-5,6-dihydrothieno[2',3':2,3]thiepino[4,5-c]pyridazin-3(2H)-one 7,7-dioxide, melting at 229°–231° C.

EXAMPLE 29

10-Bromo-2-(4-methoxyphenyl)-5,6-dihydrothieno[2',3':2,3]thiepino[4,5-c]pyridazin-3(2H)-one, melting at 230°–233° C.

EXAMPLE 30

A suspension of 2.0 g of 4-oxo-4,5,6,7-tetrahydrothieno[2,3-b]thiepin-5-acetic acid and 0.6 g of hydrazine hydrate in 20 ml of ethanol is refluxed under heating for 5 hours. After cooling, the precipitated crystals are collected by filtration and recrystallized from a mixed solvent of chloroform and ethanol to give 1.4 g of 4,4a,5,6-tetrahydrothieno[2',3':2,3]thiepino[4,5-c]pyridazin-3(2H)-one as white crystals, melting at 215°–217° C.

The following compounds can be prepared in a similar manner as the above Example 30.

EXAMPLE 31

9-Ethyl-4,4a,5,6-tetrahydrothieno[2',3':2,3]-thiepino[4,5-c]pyridazin-3(2H)-one, melting at 185°–187° C.

EXAMPLE 32

9-Methyl-4,4a,5,6-tetrahydrothieno[2',3':2,3]thiepino-[4,5-c]pyridazin-3(2H)-one, melting at 192°–193° C.

EXAMPLE 33

To a solution of 3.7 g of 9-ethyl-4,4a,5,6-tetrahydrothieno[2',3':2,3]thiepino[4,5-c]pyridazin-3(2H)-one in 40 ml of acetic acid is added dropwise a solution of 2.3 g of bromine in 10 ml of acetic acid with stirring for 15 minutes at 45°–50° C. and the mixture is stirred for 30 minutes at the same temperature. Then, the mixture is poured into ice-cold water and the precipitated crystals are collected by filtration and washed with water. The resulting crude crystals are dissolved in chloroform, subjected to column chromatography on silica gel and eluted with a mixed solvent of chloroform and ethanol (100:0.5). The crystals obtained from the fraction are recrystallized from a mixed solvent of chloroform and ethanol to give 1.8 g of 9-ethyl-5,6-dihydrothieno[2',3':2,3]thiepino[4,5-c]pyridazin-3(2H)-one as white crystals, melting at 256°–258° C.

The following compounds can be prepared in a similar manner as the above Example 33.

EXAMPLE 34

9-Methyl-5,6-dihydrothieno[2',3':2,3]thiepino[4,5-c]pyridazin-3(2H)-one, melting at 268°–270° C.

EXAMPLE 35

9-Bromo-5,6-dihydrothieno[2',3':2,3]thiepino[4,5-c]pyridazin-3(2H)-one, melting at 239°–240° C. with decomposition.

EXAMPLE 36

To a solution of 0.6 g of 9-ethyl-5,6-dihydrothieno[2',3':2,3]thiepino[4,5-c]pyridazin-3(2H)-one in 15 ml of N,N-dimethylformamide is added 0.11 g of 60% sodium hydride with stirring under ice-cooling and the mixture is stirred for 10 minutes at room temperature. To the mixture is added 0.39 g of methyl iodide, and the mixture is further stirred for 20 minutes and then poured into ice-cold water. The precipitated crystals are collected by filtration, washed with water and recrystallized from ethanol to give 0.3 g of 9-ethyl-2-methyl-5,6-dihydrothieno[2',3':2,3]thiepino[4,5-c]pyridazin-3(2H)-one as white crystals, melting at 168°–170° C.

EXAMPLE 37

The reaction and procedure are conducted in the same manner as in Example 36 using benzyl bromide in place of methyl iodide as used in Example 36 to give 2-benzyl-9-ethyl-5,6-dihydrothieno[2',3':2,3]-thiepino[4,5-c]pyridazin-3(2H)-one as pale yellow oil.

$^1$H-NMR(CDCl$_3$), δ (ppm): 1.34 (3H, t), 2.76 (2H, t), 2.84 (2H, q), 3.28 (2H, t), 5.33 (2H, s), 6.81 (1H, s), 6.94 (1H, s), 7.1–7.6 (5H, m), MS m/e: 354(M+).

IR ν (neat)cm$^{-1}$: 1670 (C=O).

EXAMPLE 38

The reaction and procedure are conducted in the same manner as in Example 36 using ethyl bromide in place of methyl iodide and using 9-bromo-5,6-dihydrothieno[2',3':2,3]thiepino[4,5-c]pyridazin-3(2H)-one in place of 9-ethyl-5,6-dihydrothieno[2',3':2,3]-thiepino[4,5-c]pyridazin-3(2H)-one as used in Example 36 to give 9-bromo-2-ethyl-5,6-dihydrothieno[2',3':2,3]-thiepino[4,5-c]pyridazin-3(2H)-one as white crystals, melting at 149°–151° C.

EXAMPLE 39

The reaction and procedure are conducted in the same manner as in Example 36 using 4-chlorobenzylchloride in place of methyl iodide and using 9-bromo-5,6-dihydrothieno[2',3':2,3]thiepino[4,5-c]pyridazin-3(2H)-one in place of 9-ethyl-5,6-dihydrothieno[2',3':2,3]thiepino[4,5-c]pyridazin-3(2H)-one as used in Example 36 to give 9-bromo-2-(4-chlorobenzyl)-5,6-dihydrothieno[2',3':2,3]thiepino[4,5-c]pyridazin-3(2H)-one as white crystals, melting at 152°–154° C.

EXAMPLE 40

A mixture of 1.4 g of 4-oxo-4,5,6,7-tetrahydrothieno[2,3-b]thiepin-5-acetic acid and 1.5 g of 2-hydroxyethylhydrazine in 50 ml of ethanol is refluxed under heating for 10 hours. After the mixture is concentrated, to the residue is added water and the mixture is extracted with ethyl acetate. The extract is washed with water, dried over magnesium sulfate and concentrated. To the residue is added isopropyl ether and the solution is allowed to stand. The precipitated crystals are collected by filtration and recrystallized from isopropyl alcohol to give 1.7 g of 9-(2-hydroxyethyl)-4,4a,5,6-tetrahydrothieno[2',3':2,3]thiepino[4,5-c]pyridazin-3(2H)-one as pale yellow crystals, melting at 165°–167° C.

EXAMPLE 41

A mixture of 1.0 g of 9-(2-hydroxyethyl)-4,4a,5,6-tetrahydrothieno[2',3':2,3]thiepino[4,5-c]pyridazin-3(2H)-one, 2 ml of triethylamine and 2 ml of acetic anhydride in 20 ml of toluene is kept on a water bath at 80°–85° C. for 3 hours. After cooling, to the mixture is added water, the organic layer is collected by a separatory funnel and concentrated. To the residue is added hexane and the precipitated crystals are collected by filtration. The resulting crystals are recrystallized from isopropyl ether to give 0.5 g of 9-(2-acetoxyethyl)-4,4a,5,6-tetrahydrothieno[2',3':2,3]thiepino[4,5-c]pyridazin-3(2H)-one as white crystals, melting at 106°–108° C.

EXAMPLE 42

A solution of 3.7 g of 4-oxo-4,5,6,7-tetrahydrothieno[2,3-b]thiepin-5-acetic acid and 2.6 g of 4-chlorophenylhydrazine in 50 ml of ethanol is refluxed under heating for 6.5 hours. Then, the reaction mixture is concentrated under reduced pressure. The resulting residue is dissolved in 40 ml of acetic acid and the solution is refluxed under heating for 1.5 hours. After cooling, the reaction mixture is concentrated under reduced pressure, the residue is subjected to column chromatography on silica gel and eluted with chloroform. The crystals obtained from the fraction are recrystallized from a mixed solvent of chloroform and ethanol to give 1.7 g of 2-(4-chlorophenyl)-4,4a,5,6-tetrahydrothieno[2',3':2,3]thiepino[4,5-c]pyridazin-3(2H)-one as pale brown crystals, melting at 134°–135° C.

EXAMPLE 43

To a solution of 5.4 g of 2-(4-chlorophenyl)-4,4a,5,6-tetrahydrothieno[2',3':2,3]thiepino[4,5-c]pyridazin-3(2H)-one in 60 ml of acetic acid is added 3.5 ml of 30% aqueous hydrogen peroxide solution under ice-cooling and stirred at the same temperature for 3 hours. Furthermore, to the solution is added 2 ml of 30% aqueous hydrogen peroxide solution and stirred for 2 hours. To the solution is additionally added 2 ml of aqueous 30% hydrogen peroxide solution, stirred for 2 hours and the mixture is poured into ice-cold water. The mixture is extracted with chloroform three times, the extract is washed with water and saline solution and dried over magnesium sulfate. The chloroform is distilled off to give 7 g of 2-(4-chlorophenyl)-4,4a,5,6-tetrahydrothieno[2',3':2,3]thiepino[4,5-c]pyridazin-3(2H)-one 7-oxide as pale brawn oil.

EXAMPLE 44

A solution of 5.6 g of 2-(4-chlorophenyl)-4,4a,5,6-tetrahydrothieno[2',3':2,3]thiepino[4,5-c]pyridazin-3(2H)-one 7-oxide in 50 ml of methanesulfonic acid is kept at 60° C. for 2 hours. The mixture is poured into ice-cold water and extracted with chloroform. The extract is washed with water, dried over magnesium sulfate and the chloroform is distilled off. The resulting residue is subjected to column chromatography on silica gel and eluted with a mixed solvent of chloroform and methanol (100:1). The crude crystals obtained from the fraction are recrystallized from ethyl acetate to 2.2 g of 2-(4-chlorophenyl)-5,6-dihydrothieno[2',3':2,3]-thiepino[4,5-c]pyridazin-3(2H)-one as white crystals, melting at 140°-143° C.

EXAMPLE 45

To a mixture of 50 ml of methylene chloride and 1.9 g of aluminum chloride is added 1.0 ml of acetyl chloride with stirring under ice-cooling and then the mixture is stirred at room temperature for 10 minutes. To the mixture is further added 2.0 g of 2-(4-chlorophenyl)-5,6-dihydrothieno[2',3':2,3]thiepino[4,5-c]pyridazin-3(2H)-one under ice-cooling and the mixture is stirred for 3 hours at room temperature. To the mixture is added water and the solution is extracted with chloroform. The extract is washed with water, dried over magnesium sulfate and concentrated under reduced pressure. The resulting crystals are recrystallized from a mixed solvent of chloroform and ethanol to give 2.0 g of 9-acetyl-2-(4-chlorophenyl)-5,6-dihydrothieno[2',3':2,3]thiepino[4,5-c]pyridazin-3(2H)-one, as white crystals, melting at 248°-250° C.

EXAMPLE 46

The reaction and procedure are conducted in the same manner as in Example 45 using benzoylchloride in place of acetylchloride as used in Example 45 to give 9-benzoyl-2-(4-chlorophenyl)-5,6-dihydrothieno[2',3':2,3]thiepino[4,5-c]pyridazin-3(2H)-one as white crystals, melting at 180°-182° C.

EXAMPLE 47

The reaction and procedure are conducted in the same manner as in Example 45 using chloroacetylchloride in place of acetylchloride as used in Example 45 to give 9-chloroacetyl-2-(4-chlorophenyl)-5,6-dihydrothieno[2',3':2,3]thiepino[4,5-c]pyridazin-3(2H)-one as white crystals, melting at 178°-180° C.

EXAMPLE 48

To a solution of 0.7 g of 9-acetyl-2-(4-chlorophenyl)-5,6-dihydrothieno[2',3':2,3]thiepino[4,5-c]pyridazin-3(2H)-one obtained in Example 45 in 100 ml of formic acid is added 0.7 ml of hydrogen peroxide with stirring at room temperature. The mixture is stirred for 2 hours at room temperature, poured into ice-cold water and extracted with chloroform. The extract is washed with water, dried and concentrated under reduced pressure. The resulting crystals are recrystallized from a mixed solvent of chloroform and methanol to give 0.6 g of 9-acetyl-2-(4-chlorophenyl)-5,6-dihydrothieno[2',3':2,3]thiepino[4,5-c]pyridazin-3(2H)-one 7,7-dioxide, melting at 272°-273° C. with decomposition.

EXAMPLE 49

The reaction and procedure are conducted in the same manner as in Example 48 using 9-benzoyl-2-(4-chlorophenyl)-5,6-dihydrothieno[2',3':2,3]thiepino[4,5-c]pyridazin-3(2H)-one obtained in Example 46 in place of 9-acetyl-2-(4-chlorophenyl)-5,6-dihydrothieno[2',3':2,3]thiepino[4,5-c]pyridazin-3(2H)-one as used in Example 48 to give 9-benzoyl-2-(4-chlorophenyl)-5,6-dihydrothieno[2',3':2,3]thiepino[4,5-c]pyridazin-3(2H)-one 7,7-dioxide as white crystals, melting at 254°-256° C.

EXAMPLE 50

To a solution of 0.5 g of 9-acetyl-2-(4-chlorophenyl)-5,6-dihydrothieno[2',3':2,3]thiepino[4,5-c]pyridazin-3(2H)-one 7,7-dioxide obtained in Example 48 in a mixed solvent of 40 ml of methanol and 30 ml of chloroform is added 0.1 g of sodium borohydride under ice-cooling and the mixture is stirred for 30 minutes at room temperature. After the completion of reaction, to the mixture is added water and the solution is extracted with chloroform. The extract is washed with water, dried and concentrated under reduced pressure. The resulting crystals are recrystallized with ethanol to give 0.25 g of 2-(4-chlorophenyl)-9-(1-hydroxyethyl)-5,6-dihydrothieno[2',3':2,3]thiepino[4,5-c]pyridazin-3(2H)-one 7,7-dioxide as white crystals, melting at 233°-235° C.

EXAMPLE 51

To a suspension of 3.2 g of 9-chloroacetyl-2-(4-chlorophenyl)-5,6-dihydrothieno[2',3':2,3]thiepino[4,5-c]pyridazin-3(2H)-one obtained in Example 47 in 40 ml of acetic acid is added 6.0 g of potassium acetate and the mixture is refluxed under heating for 3 hours with stirring. After cooling, to the mixture is added water and the solution is extracted with chloroform. The extract is washed with water, dried and concentrated under reduced pressure. The resulting residue is subjected to column chromatography on silica gel and eluted with a mixed solvent of chloroform and methanol (99:1). The crystals obtained from the fraction are recrystallized from a mixed solvent of chloroform and ethanol to give 9-acetyloxyacetyl-2-(4-chlorophenyl)-5,6-dihydrothieno[2',3':2,3]thiepino[4,5-c]pyridazin-3(2H)-one as white crystals, melting at 172°-174° C.

EXAMPLE 52

To a solution of 2.8 g of 9-acetyloxyacetyl-2-(4-chlorophenyl)-5,6-dihydrothieno[2',3':2,3]thiepino[4,5-c]pyridazin-3(2H)-one obtained in Example 51 in 40 ml of trifluoroacetic acid is added 3.0 ml of triethylsilane and the mixture is stirred for 5 hours at room temperature. After the completion of reaction, to the mixture is added water and the solution is extracted with chloroform. The extract is washed, dried and concentrated under reduced pressure. The resulting residue is subjected to column chromatography on silica gel and eluted with a mixed solvent of chloroform and methanol (99:1). The crystals obtained from the fraction are recrystallized from a mixed solvent of chloroform and ethanol to give 1.0 g of 9-(2-acetoxyethyl)-2-(4-chlorophenyl)-5,6-dihydrothieno[2',3':2,3]thiepino[4,5-c]pyridazin-3(2H)-one as white crystals, melting at 115°–117° C.

EXAMPLE 53

The reaction and procedure are conducted in the same manner as in Example 48 using 9-(2-acetoxyethyl)-2-(4-chlorophenyl)-5,6-dihydrothieno[2',3':2,3]thiepino[4,5-c]pyridazin-3(2H)-one obtained in Example 52 in place of 9-acetyl-2-(4-chlorophenyl)-5,6-dihydrothieno[2',3':2,3]thiepino[4,5-c]pyridazin-3(2H)-one as used in Example 48 to give 9-(2-acetoxyethyl)-2-(4-chlorophenyl)-5,6-dihydrothieno[2',3':2,3]thiepino[4,5-c]pyridazin-3(2H)-one 7,7-dioxide, melting at 137°–140° C.

EXAMPLE 54

To a suspension of 10 g of 2-ethyl-5-oxo-5,6-dihydro-4H-thieno[2,3-b]thiopyran-5-acetic acid in 150 ml of toluene is added 6.7 g of 4-chlorophenylhydrazine and the mixture is refluxed under heating removing water over 15 hours. After cooling, the mixture is concentrated under reduced pressure. The residue is subjected to column chromatography on silica gel and eluted with chloroform. The crystals obtained from the fraction are recrystallized from a mixed solvent of chloroform and ethanol to give 10 g of 2-(4-chlorophenyl)-8-ethyl-4a,5-dihydro-2H-thieno[2',3':2,3]thiopyrano[4,5-c]pyridazin-3(4H)-one as pale yellow crystals, melting at 138°–141° C.

EXAMPLE 55

To a solution of 5 g of 2-(4-chlorophenyl)-8-ethyl-4a,5-dihydro-2H-thieno[2',3':2,3]thiopyrano[4,5-c]pyridazin-3(4H)-one in a 30% solution of hydrogen bromide in acetic acid is added 2 ml of dimethylsulfoxide at room temperature. After the mixture is stirred for an hour at the same temperature, the mixture is poured into ice-cold water and extracted with chloroform. The extract is washed with water, dried over magnesium sulfate and concentrated under reduced pressure. The resulting crystals are recrystallized from a mixed solvent of chloroform and ethanol to give 3.5 g of 2-(4-chlorophenyl)-8-ethyl-5H-thieno[2',3':2,3]thiopyrano[4,5-c]pyridazin-3(2H)-one as yellow needles, melting at 161°–163° C.

EXAMPLE 56

To a solution of 1.5 g of 2-(4-chlorophenyl)-8-ethyl-5H-thieno[2',3':2,3]thiopyrano[4,5-c]pyridazin-3(2H)-one in a mixed solvent of 30 ml of formic acid and 30 ml of chloroform is added 1.5 ml of 30% hydrogen peroxide and the mixture is stirred for 7 hours at room temperature. To the mixture is added water and the solution is extracted with chloroform. The extract is washed with water, dried over magnesium sulfate and concentrated under reduced pressure. The resulting residue is subjected to column chromatography on silica gel and eluted with a mixed solvent of chloroform and methanol (98:2). The crystals obtained from the fraction are recrystallized from a mixed solvent of chloroform and ethanol to give 0.75 g of 2-(4-chlorophenyl)-8-ethyl-5H-thieno[2',3':2,3]thiopyrano[4,5-c]pyridazin-3(2H)-one 6,6-dioxide as pale yellow needles, melting at 189°–191° C.

EXAMPLE 57

The reaction and procedure are conducted in the same manner as in Example 44 using 9-bromo-2-(4-methoxyphenyl)-4,4a,5,6-tetrahydrothieno[2',3':2,3]thiepino[4,5-c]pyridazin-3(2H)-one 7-oxide in place of 2-(4-chlorophenyl)-4,4a,5,6-tetrahydrothieno[2',3':2,3]thiepino[4,5-c]pyridazin-3(2H)-one 7-oxide as used in Example 44 to give 9-bromo-2-(4-methoxyphenyl)-5,6-dihydrothieno[2',3':2,3]thiepino[4,5-c]pyridazin-3(2H)-one as white crystals, melting at 148°–150° C.

EXAMPLE 58

The reaction and procedure are conducted in the same manner as in Example 44 using 9-ethyl-2-(4-methoxyphenyl)-4,4a,5,6-tetrahydrothieno[2',3':2,3]thiepino[4,5-c]pyridazin-3(2H)-one 7-oxide in place of 2-(4-chlorophenyl)-4,4a,5,6-tetrahydrothieno[2',3':2,3]thiepino[4,5-c]pyridazin-3(2H)-one 7-oxide as used in Example 44 to give 9-ethyl-2-(4-methoxyphenyl)-5,6-dihydrothieno[2',3':2,3]thiepino[4,5-c]pyridazin-3(2H)-one as white crystals, melting at 141°–143° C.

EXAMPLE 59

The reaction and procedure are conducted in the same manner as in Example 44 using 2-(4-methoxyphenyl)-9-methyl-4,4a,5,6-tetrahydrothieno[2',3':2,3]thiepino[4,5-c]pyridazin-3(2H)-one 7-oxide in place of 2-(4-chlorophenyl)-4,4a,5,6-tetrahydrothieno[2',3':2,3]thiepino[4,5-c]pyridazin-3(2H)-one 7-oxide as used in Example 44 to give 2-(4-methoxyphenyl)-9-methyl-5,6-dihydrothieno[2',3':2,3]thiepino[4,5-c]pyridazin-3(2H)-one as white crystals, melting at 145°–146° C.

EXAMPLE 60

To a solution of 14.8 g of 2-(4-methoxyphenyl)-4,4a,5,6-tetrahydrothieno[2',3':2,3]thiepino[4,5-c]pyridazin-3(2H)-one in 100 ml of 30% hydrogen bromide-acetic acid is added 6.1 ml of dimethylsulfoxide with stirring at room temperature. The mixture is stirred for 4 hours at room temperature, poured into ice-cold water and extracted with chloroform. The extract is washed with water, dried and concentrated under reduced pressure. The resulting crystals are recrystallized from a mixed solvent of toluene and isopropyl ether to give 10 g of 2-(4-methoxyphenyl)-5,6-dihydrothieno[2',3':2,3]thiepino[4,5-c]pyridazin-3(2H)-one as white crystals, melting at 126°–128° C.

The following compounds can be prepared in a similar manner as the above examples.

EXAMPLE 61

2-(4-Chlorophenyl)-5,6-dihydrothieno[2',3':2,3]thiepino[4,5-c]pyridazin-3(2H)-one 7-oxide, melting at 184°–186° C. with decomposition.

EXAMPLE 62

2-(4-Chlorophenyl)-5,6-dihydrothieno[2',3':2,3]thiepino[4,5-c]pyridazin-3(2H)-one 7,7-dioxide, melting at 277°–279° C.

EXAMPLE 63

2-(4-Chlorophenyl)-9-methyl-5,6-dihydro-thieno[2',3':2,3]thiepino[4,5-c]pyridazin-3(2H)-one 7,7-dioxide, melting at 241°-243° C.

EXAMPLE 64

9-Ethyl-2-(4-methoxyphenyl)-5,6-dihydro-thieno[2',3':2,3]thiepino[4,5-c]pyridazin-3(2H)-one 7,7-dioxide, melting at 221°-223° C.

EXAMPLE 65

9-Bromo-2-(4-chlorophenyl)-5,6-dihydro-thieno[2',3':2,3]thiepino[4,5-c]pyridazin-3(2H)-one 7,7-dioxide, melting at 235°-237° C.

EXAMPLE 66

2-(4-Methoxyphenyl)-9-methyl-5,6-dihydro-thieno[2',3':2,3]thiepino[4,5-c]pyridazin-3(2H)-one 7-oxide, melting at 159°-161° C. with decomposition.

EXAMPLE 67

2-(4-Methoxyphenyl)-9-methyl-5,6-dihydro-thieno[2',3':2,3]thiepino[4,5-c]pyridazin-3(2H)-one 7,7-dioxide, melting at 242°-244° C.

EXAMPLE 68

2-(4-Methoxyphenyl)-4,4a,5,6-tetrahydro-thieno[2',3':2,3]thiepino[4,5-c]pyridazin-3(2H)-one, melting at 144°-146° C.

EXAMPLE 69

2-(4-Chlorophenyl)-9-propyl-5,6-dihydro-thieno[2',3':2,3]thiepino[4,5-c]pyridazin-3(2H)-one, melting at 136°-137° C.

EXAMPLE 70

2-(4-Chlorophenyl)-9-propyl-5,6-dihydro-thieno[2',3':2,3]thiepino[4,5-c]pyridazin-3(2H)-one 7-oxide, melting at 149°-151° C.

EXAMPLE 71

2-(4-Chlorophenyl)-9-propyl-5,6-dihydro-thieno[2',3':2,3]thiepino[4,5-c]pyridazin-3(2H)-one 7,7-dioxide, melting at 222°-224° C.

EXAMPLE 72

9-Butyl-2-(4-chlorophenyl)-5,6-dihydro-thieno[2',3':2,3]thiepino[4,5-c]pyridazin-3(2H)-one, melting at 125°-130° C.

EXAMPLE 73

9-Butyl-2-(4-chlorophenyl)-5,6-dihydro-thieno[2',3':2,3]thiepino [4,5-c]pyridazin-3(2H)-one 7,7-dioxide, melting at 184°-186° C.

While the present invention has been adequately and sufficiently described in the foregoing specification including examples, the description can be changed or modified within the spirit and scope of this invention.

What is claimed is:

1. A thiophene compound of the formula:

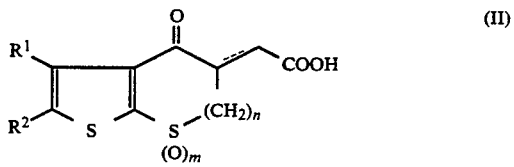

wherein $R^1$ is hydrogen, nitro, amino, halogen or $C_{1-4}$ alkyl; $R^2$ is hydrogen, nitro, amino, halogen, $C_{1-4}$ alkyl, $C_{1-4}$ haloalkyl, acyl which is selected from the group consisting of acetyl, propionyl, butyryl, isobutyryl, pivaloyl, phenylacetyl, 3-phenyl-propionyl, 2-phenyl-propionyl, benzoyl, 1-naphthoyl, 2-naphthoyl, nicotinoyl, isonicotinoyl, 2-thenoyl, 3-thenoyl, 2-furoyl, 3-furoyl, and the aforementioned acyl which is substituted on the aromatic ring by one substituent selected from the group consisting of halogen, hydroxy, amino, nitro, cyano, $C_{1-4}$ alkyl, $C_{1-4}$ alkoxy and carboxyl, $C_{2-5}$ alkoxycarbonyl, $C_{1-4}$ alkoxy-$C_{1-4}$ alkyl, aryloxy-$C_{1-4}$ alkyl, acyloxy-$C_{1-4}$ alkyl which is selected from the group consisting of acetoxymethyl, propionyloxymethyl, 1- or 2-acetoxyethyl, 1- or 2-propionyloxyethyl, 3-acetoxypropyl, 3-propionyloxypropyl, benzoyloxymethyl, 2-benzoyloxyethyl, 3-benzoyloxypropyl, 4-benzoyloxybutyl, hydroxy-$C_{1-4}$ alkyl, acyloxy-$C_{2-5}$ alkanoyl which is selected from the group consisting of acetoxyacetyl, 3-acetoxypropionyl, 4-acetoxybutyryl, benzoyloxyacetyl, 3-benzoyloxypropionyl and 4-benzoyloxybutyryl, $C_{1-4}$ alkoxy-$C_{2-5}$ alkanoyl, hydroxy-$C_{2-5}$ alkanoyl, aryloxy-$C_{2-5}$ alkanoyl or $C_{2-5}$ haloalkanoyl;

m is 0, 1 or 2;

n is 2; and the bond represented by ==== is a single bond or a double bond.

2. A compound of claim 1 selected from the group consisting of, 4-oxo-4,5,6,7-tetrahydrothieno[2,3-b]thiepin-5-acetic acid, 2-methyl-4-oxo-4,5,6,7-tetrahydrothieno[2,3-b]thiepin-5-acetic acid, 2-ethyl-4-oxo-4,5,6,7-tetrahydrothieno[2,3-b]thiepin-5-acetic acid, 2-bromo-4-oxo-4,5,6,7-tetrahydrothieno[2,3-b]thiepin-5-acetic acid and, 4-oxo-2-propyl-4,5,6,7-tetrahydrothieno[2,3-b]thiepin-5-acetic acid.

* * * * *